United States Patent [19]

O'Young et al.

[11] Patent Number: 5,597,944
[45] Date of Patent: Jan. 28, 1997

[54] DEHYDROGENATION OF N-PARAFFIN TO N-OLEFIN EMPLOYING MANGANESE OXIDE OCTAHEDRAL MOLECULAR SIEVE AS CATALYST

[75] Inventors: Chi-Lin O'Young, Poughkeepsie; Robert A. Sawicki, Stormville, both of N.Y.; Yuan-Gen Yin, Mainsfield, Conn.; Wen-Qing Xu, Williantic, Conn.; Steven L. Suib, Storrs, Conn.

[73] Assignee: Texaco Inc., White Plains, N.Y.

[21] Appl. No.: 335,317

[22] Filed: Nov. 7, 1994

[51] Int. Cl.$^6$ ............................ C07C 5/333; C07C 5/327
[52] U.S. Cl. ............................ 585/654; 585/661; 585/662
[58] Field of Search ............................ 585/654, 661, 585/662

[56] References Cited

U.S. PATENT DOCUMENTS 5,095,166  3/1992  Forschner et al. .............. 585/653
5,340,562  8/1994  O'Young et al. ................ 423/599

*Primary Examiner*—Mark L. Bell
*Assistant Examiner*—Salim G. Bared
*Attorney, Agent, or Firm*—Kenneth R. Priem; Dominick G. Vicari; George J. Darsa

[57] ABSTRACT

The dehydrogenation of n-parrofins to n-olefins is catalyzed by novel synthetic manganese oxide octahedral molecular sieves such as OMS-1 and OMS-2.

20 Claims, 1 Drawing Sheet

DEHYDROGENATION OF N-PARAFFIN TO N-OLEFIN EMPLOYING MANGANESE OXIDE OCTAHEDRAL MOLECULAR SIEVE AS CATALYST

BACKGROUND OF THE INVENTION

This invention relates to a process for producing n-olefins via the dehydrogenation of n-paraffins. More particularly, this invention relates to the preparation of an n-olefin having from about 5 to about 20 carbon atoms by dehydrogenating an n-paraffin having this number of Carbons in the presence of manganese oxide octahedral molecular sieve (OMS) as catalyst.

Olefins having from about 5 to about 20 carbon atoms have been prepared by a number of commercial methods including thermal and catalytic cracking of petroleum fractions, thermal cracking of paraffin wax, dehydrochlorination of monochlorinated paraffinic hydrocarbons, polymerization of low molecular weight olefins by the Ziegler process, hydrogenation of fatty acids to alcohols with subsequent dehydration of the alcohol to the olefin, fractionation of natural oils and resins of plants and catalytic dehydrogenation of saturated hydrocarbons.

Straight-chain olefin compounds having from about 5 to about 20 carbon atoms have a variety of uses. They may be used for the synthesis of other compounds such as aldehydes, alcohols, acids and mercaptans. In addition, they are also valuable in the preparation of synthetic detergents, synthetic rubber and resins and can be employed as lubricating oil additives.

Manganese oxide octahedral molecular sieves (OMS) possessing mono-directional tunnel structures constitute a family of molecular sieves wherein chains of $MnO_6$ octahedra share edges to form tunnel structures of varying sizes. Such materials have been detected in samples of terrestrial origin and are also found in manganese nodules recovered from the ocean floor. Manganese nodules have been described as useful catalysts in the oxidation of carbon monoxide, methane and butane (U.S. Pat. No. 3,214,236), the reduction of nitric oxide with ammonia (*Atmospheric Environment*, Vol. 6, p. 309 (1972)) and the demetallation of topped crude in the presence of hydrogen (*Ind. Eng. Chem. Proc. Dev.l*, Vol. 13, p. 315 (1974)).

The hollandites are naturally occurring hydrous manganese oxides with tunnel structures (also described as "framework hydrates") in which Mn can be present as $Mn^{4+}$ and other oxidation states, the tunnels can vary in size and configuration and various mono- or divalent cations can be present in the tunnels. The hollandite structure consists of double chains of $MnO_6$ octahedra which share edges to form (2×2) tunnel structures. The average size of these tunnels is about 4.6 Å square. Ba, K, Na and Pb ions are present in the tunnels and coordinated to the oxygens of the double chains. The identity of the tunnel cations determines the mineral species. Specific hollandite species include hollandite ($BaMn_8O_{16}$). cryptomelane ($KMn_8 O_{16}$), manjiroite ($NaMn_8O_{16}$) and coronadite ($PbMn_8 O_{16}$).

The hydrothermal method of synthesizing a manganese oxide octahedral molecular sieve possessing (2×2) tunnel structures similar to the naturally-occurring hollandites is described in "Hydrothermal Synthesis of Manganese Oxides with Tunnel Structures," in *Synthesis of Microporous Materials*, Vol. II, 333, M. L. Occelli, H. E. Robson Eds. Van Nostrand Reinhold, N.Y., 1992. Such synthetic octahedral molecular sieves having (2×2) tunnel structures are referred to in the art by the designation OMS-2. The (2×2) tunnel structure of OMS-2 is diagrammtically depicted in FIG. 1A.

The hydrothermal method of producing OMS-2 involves autoclaving an aqueous solution of manganese cation and permanganate anion under acidic conditions, i.e., pH<3, at temperatures ranging from about 80° to about 140° C. in the presence of counter cations having ionic diameters of between about 2.3 and about 4.6 Å. The counter cations serve as templates for the formation of OMS-2 product and can be retained in the tunnel structures thereof. Based on analytical tests, OMS-2 produced via this method is thermally stable up to about 600° C.

Alternatively, OMS-2 can be produced by the method disclosed in R. Giovanili and B. Balmer, *Chimia*, 35 (1981) 53. Thus, when manganese cation and permanganate anion are reacted under basic conditions, i.e., pH>12, a layered manganese oxide precursor is produced. This precursor is ion exchanged to form another layered manganese oxide which is then calcined at high temperatures, i.e., temperatures generally exceeding about 600° C., to form OMS-2 product. Analytical tests indicate that OMS-2 produced via this method is thermally stable up to about 800° C. and the average oxidation state of manganese ion is lower.

The todorokites are naturally occurring manganese oxides with (3×3) tunnel structures formed by triple chains of $MnO_6$ edge-sharing octahedra. Todorokites and related species are described by Turner et al. in "Todorokites: A New Family of Naturally Occurring Manganese Oxides", *Science*, Vol. 212, pp. 1024–1026 (1981). The authors speculate that since todorokites are often found in deep-sea manganese nodules containing high concentrations of copper and nickel, it is probable that such metals substitute for $Mn^{2+}$ in the octahedral framework.

Todorokites have attracted particular interest because of their relatively large tunnel dimension and their cation-exchange behavior which is similar to that of zeolites (Shen et al., "Manganese Oxide Octahedral Molecular Sieves: Preparation, Characterization, and Applications", *Science*, Vol. 260, pp. 511–515 (1993)). The naturally occurring todorokites are poorly crystalline, impure in composition and coexist with other manganese oxide minerals. Results of high resolution transmission electron microscopy (HRTEM) show that todorokite contains random intergrowth material of 3×2, 3×3, 3×4 and 3×5 tunnel structures. Because of their disordered structure, the todorokites exhibit variable and non-reproducible catalytic activity, a drawback which militates against their commercial use.

A method of synthesizing a manganese oxide octahedral molecular sieve possessing (3×3) tunnel structures similar to the naturally-occurring todorkites is described in U.S. Pat. No. 5,340,562. Such synthetic octahedral molecular sieves having (3×3) tunnel structures are referred to in the art by the designation OMS-1. The (3×3) tunnel structure of OMS-1 is diagrammatically depicted in FIG. 1B.

OMS-1 can be prepared by reacting manganese cation and permanganate anion under strongly basic conditions to form a layered manganese oxide precursor, thereafter aging the precursor at room temperature for at least 8 hours, ion exchanging the aged precursor and then autoclaving the ion-exchanged precursor at from about 150° to about 180° C. for several days. Analytical tests indicate that OMS-1 produced via this method is thermally stable up to about 500° C.

Methods of substituting the frameworks of OMS-1 and OMS-2 with a metal other than manganese are described in commonly assigned, copending U.S. application. Ser. No. 08/215,496, filed Mar. 21, 1994.

SUMMARY OF THE INVENTION

In accordance with the present invention, the dehydrogenation of n-paraffin to n-olefin is catalyzed by a synthetic manganese oxide octahedral molecular sieve. Reaction conditions such as space velocity, temperature and pressure can be varied to optimize the production of n-olefin from n-paraffin depending on the particular OMS catalyst being employed. The catalyst itself can be any synthetic OMS possessing mono-directional tunnel structures such as those found in the naturally-occurring hollandites and todorokites, for example, OMS-2 and OMS-1. Manganese oxide octahedral molecular sieves substituted with alkali metal cation(s) such as alkali metal, alkaline earth metal and/or transition metal cation(s) in the tunnel structures thereof and/or with transition metal cation(s) in the frameworks thereof can be employed.

Unlike the naturally-occurring hollandites and todorokites, synthetic-manganese oxide octahedral molecular sieve employed as catalyst in the method of this invention possesses a highly uniform and homogeneous structure, i.e., one made up substantially entirely of a single tunnel structure species without admixture of any significant amount of other tunnel structure species. As such, synthetic manganses oxide octahedral molecular sieve utilized herein provides consistent and reproducible results, benefits which have heretofore not been attainable employing naturally-occurring manganese oxides with their mixed tunnel structure morphologies.

The term "OMS" as utilized herein shall be understood to refer to substituted and unsubstituted synthetic manganese oxide octahedral molecular sieves.

DETAILED DESCRIPTION OF THE INVENTION

Figure 1A:
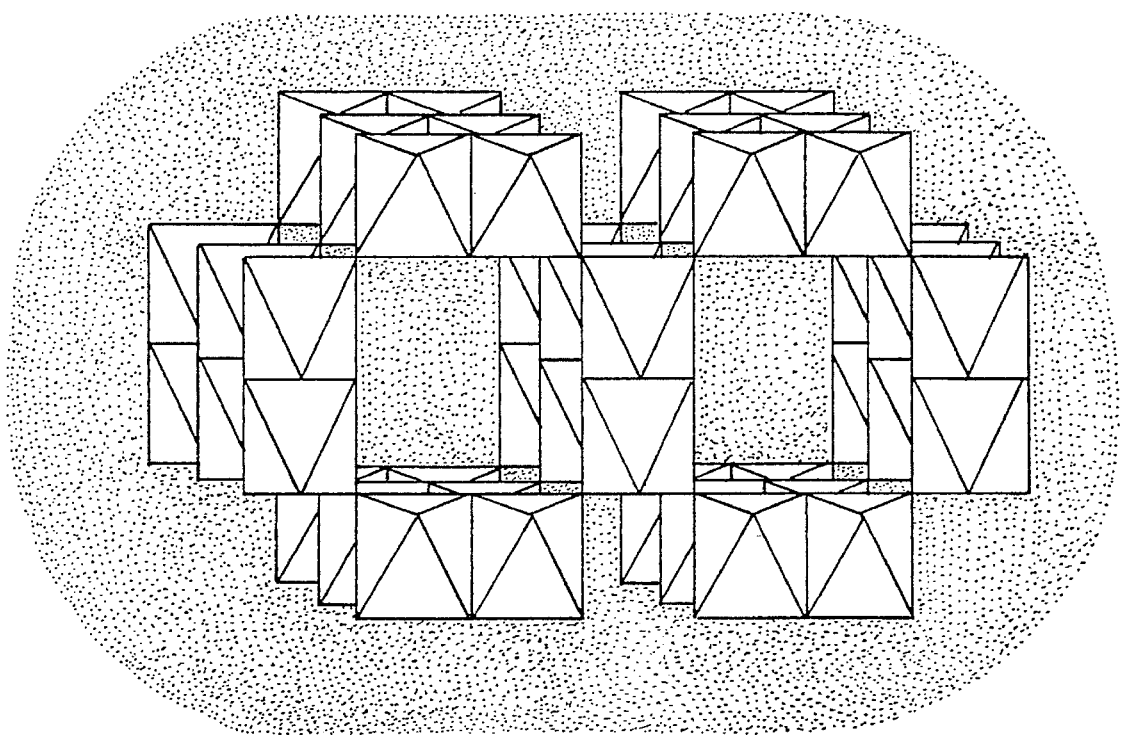
FIGS. 1A and 1B are diagrammatic representations of three-dimensional tunnel structures of OMS-2 and OMS-1, respectively.
Figure 1B:
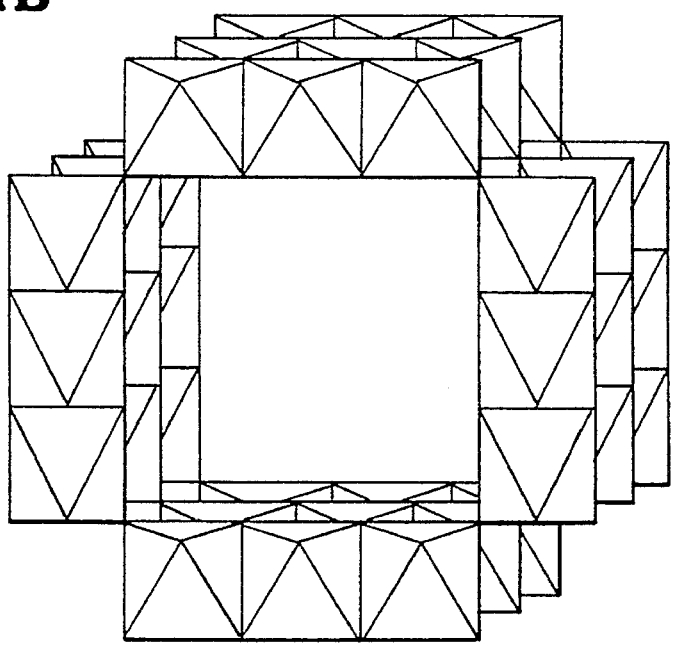

The preferred catalyst utilized herein is a synthetic tunnel-substituted and/or framework-substituted manganese oxide octahedral molecular sieve. Where OMS-2 is employed the catalyst will correspond to the general formula:

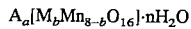

wherein A is a +1, +2, +3 or +4 tunnel cation or combination thereof, $0 \leq a \leq 4$, M is a +1, +2, +3 or +4 framework-substituting metal cation or combination thereof, $0 \leq b \leq 8$ and $n \geq 0$. Where OMS-1 is employed the catalyst will correspond to the general formula:

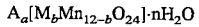

wherein A is a +1, +2, +3 or +4 tunnel cation or combination thereof, $0 \leq a \leq 6$, M is a +1, +2, +3 or +4 framework-substituting metal cation or combination thereof, $0 \leq b \leq 12$ and $n \geq 0$.

The framework-substituting metal cation(s), M, can be a transition metal selected from Groups IIIA, IVA, VA, VIA, VIIA, VIIIA, IB and IIB of the Periodic Table of the Elements. Examples of useful framework-substituting metals include Mg, Fe, Co, Ni, Cu, Ti, V, Cd, Mo, W, Cr, Zn, La, Ir, Rn, Pd and Pt. Preferred metals include Co, Cu, Ni, Zn, La and Pd. The tunnel cation(s), A, can be alkali metal, alkaline earth metal and transition metal cations which facilitate the selection, formation and stabilization of desired OMS products. Thus, the tunnel cations can serve as templates for crystallization of the products. The ionic diameters of some alkali and alkaline earth metal cations which can be employed are listed below:

| Cation | $Li^+$ | $Na^+$ | $K^+$ | $Cs^+$ | $Mg^{2+}$ | $Ca^{2+}$ | $Ba^{2+}$ |
|---|---|---|---|---|---|---|---|
| r(Å) | 1.36 | 1.96 | 2.66 | 3.78 | 1.30 | 1.98 | 2.70 |

Examples of transition metals which can be employed include Co, Ni, Cu and Zn.

The method of synthesis of a manganese oxide octahedral molecular sieve utilized herein will depend on whether OMS-1 or OMS-2 is desired. The methods of making OMS-1 and OMS-2 have in common a first step of reacting manganese cation and permanganate anion optionally together with framework-substituting metal cation(s) in an aqueous reaction medium. When the reaction is carried out under acidic conditions and autoclaved at temperatures ranging from about 80° to about 140° C. in the presence of counter cations having ionic diameters of between about 2.3 and about 4.6 Å, OMS-2 is formed. Alternatively, when the reaction is carried out under strongly basic conditions a layered manganese oxide precursor is formed. OMS-2 is formed when this precursor is ion exchanged and calcined at high temperatures. In contrast, OMS-1 is formed when this precursor is aged at room temperature for at least about 8 hours, ion exchanged and thereafter autoclaved at from about 150° to about 180° C. for several days. Examples for producing specific substituted synthetic manganese oxide octrahedral molecular sieves which may be employed in the method of this invention are presented hereinbelow.

Synthetic manganese oxide octahedral molecular sieves utilized herein can be bound within a matrix or binder, e.g., alumina, silica-alumina, clay or admixtures thereof, to provide a support for the OMS component. Normally, the composited catalyst can contain at least about 10 up to about 85 weight percent of such a binder or matrix. The alumina which can be used as the matrix material of the composited catalyst utilized in the method of the present invention can be any suitable grade of crystalline or amorphous alumina which is substantially inert.

The synthetic manganese oxide octahedral molecular sieve can be composited with the matrix or binder in a variety of ways, e.g., by adding OMS to a silica-alumina slurry, spray drying the mixture, washing the resultant product and drying. Optionally, a clay diluent can be present in the silica-alumina slurry. Such matrixes can be prepared by admixing colloidal alumina (boehmite) and colloidal silica and allowing the matrix properties to vary over a wide range from catalytically inert to active. The activity, thermal stability, surface area and pore distribution of the matrix can be controlled by varying the amounts and particle size distributions of the respective colloids. In the section by Magee and Blazek on "Zeolite Cracking Catalysts" in ACS Monograph 171, *Zeolite Chemistry and Catalysts* (J. Rabo, Ed.; Am. Chem. Soc., Wash, D.C. 1976), guidance for the preparation of zeolite catalysts containing high porosity matrixes such as silica-alumina can be found.

The synthetic manganese oxide octahedral molecular sieve catalyst can be composited with a porous clay matrix material which has suitable binding properties and is resistant to the temperature and other conditions employed in the dehydrogenation process. The composite is then calcined to confer the required physical strength. Naturally occurring clays can be composited with the OMS catalyst and these clays can be used in the raw state as originally mined or initially subjected to calcination, acid treatment, chemical modification or purification.

Examples of suitable clays which can be used include the bentonite and kaolin families. Bentonites are mixtures of clays, mainly montmorillonites, which may also contain kaolinite clays. The Wyoming bentonites and montmorillonites are preferred because of their relatively high purity. Kaolin clays include, for example, the Dixie, McNamee-Georgia and Florida clays and others in which the main mineral constituent is halloysite, kaolinite, dickite, nacrite or anuxite. Other clays may also be found to be suitable for use in the present process.

The amount of clay or other matrix material relative to OMS in the composite will determine, to a certain extent, the physical strength of the final catalyst, especially its attrition resistance and crushing strength. The mechanical properties of the catalyst can therefore be modified by appropriate choice of matrix/OMS ratio, with greater amounts of matrix generally conferring better mechanical properties. On the other hand, larger amounts of matrix mean that less of the OMS catalyst with its desired attendant properties will be available to participate in the eventual dehydrogenation reaction. A balance will therefore be struck, in most cases, between activity and mechanical properties. Normally, the amount of matrix material will not exceed 50 percent by weight of the composite and in most cases it will not exceed 40 percent by weight and may be lower, e.g., 25 percent by weight or even 15 percent by weight.

The synthetic manganese oxide octahedral molecular sieve catalyst may conveniently be composited with the clay or other matrix materials by forming an aqueous slurry of OMS with the matrix material, spray drying the slurry to form microspheres and then calcining. Alternatively, extrudates, pellets and beads can be formed from matrix and OMS mixtures.

Preferably, the hydrocarbons selected as feedstock for the dehydrogenation process herein are normal paraffin hydrocarbons having from about 5 to about 20 carbon atoms. The n-paraffin hydrocarbon feedstock can contain one n-paraffin hydrocarbon or a mixture thereof. Petroleum fractions containing substantial amounts of n-paraffin hydrocarbons include primary flash distillates, naphthas, kerosine, diesel fuel, furnace oil and other petroleum distillate fractions. Such petroleum fractions can be treated to separate those n-paraffin fractions which are desired. Any well known treatment for carrying out such a separation procedure can be employed, e.g., distillation, adsorption-desorption, etc.

Reaction temperatures for the catalytic dehydrogenation of n-paraffin hydrocarbons can range from about 100° to about 750° C., preferably from about 400° to about 650° C. Since the dehydrogenation reaction is endothermic, heat must be continually added to the reaction in order to maintain the reaction. Such heat is generally supplied by preheating the feedstock to a temperature sufficient to maintain the desired temperature in the dehydrogenation zone. Such preheat can be obtained by heat exchange between reaction effluent and reaction charge and by heating reaction charge in a heating means such as an oil or gas-fired heater.

Moderate reaction pressures are employed for the dehydrogenation of n-paraffin hydrocarbons into n-olefin hydrocarbons. Pressures ranging from about 0.1 to about 100 atm, preferably from about 0.2 to about 10 atm, can be employed.

Contact time between n-paraffin hydrocarbons and the manganese oxide octahedral molecular catalyst is generally maintained for a relatively short period of time. Weight hourly space velocities (WHSV) of from about 0.1 to about 40, preferably from about 0.2 to about 25, can be employed. When n-paraffin hydrocarbons are maintained in the presence of OMS catalyst for extended periods of time, unwanted side reactions tend to increase. Thus, e.g., side reactions such as polymerization of n-olefin product, deposition of coke upon the OMS catalyst, cracking of n-paraffin hydrocarbons into lower molecular weight hydrocarbons, etc., increase as contact time between reactant hydrocarbons and OMS catalyst is increased.

Commonly, excess molecular hydrogen is supplied with the reactant n-paraffin hydrocarbons to the dehydrogenation zone. Such excess hydrogen tends to reduce the rate of coke deposition upon the OMS catalyst. Since the dehydrogenation reaction produces hydrogen, a portion of the hydrogen separated from the dehydrogenation zone effluent can be recycled for admixture with additional n-paraffin hydrocarbon charge to maintain the desired hydrogen to hydrocarbon ratio in the dehydrogenation zone. Excess hydrogen produced in the dehydrogenation zone can be recovered for use as fuel or in other refinery operations or it can be vented to a flare for disposal. Mole ratios of hydrogen to hydrocarbon in the feedstock ranging from about 0 to about 10, preferably from about 0.5 to about 6, can be employed.

During the course of a continuous dehydrogenation process for the conversion of n-paraffin hydrocarbons into n-olefin hydrocarbons, coke and/or other carbonaceous deposits accumulate upon the surface and within the pores of the dehydrogenation catalyst. As such accumulations increase, the activity of the catalyst to dehydrogenate the paraffin hydrocarbons decreases. After a time of continuous operation, the accumulation of carbonaceous deposits will become so great and the catalytic activity of the catalyst will be so low that it is uneconomical to continue operation of the dehydrogenation process. The catalytic activity of a dehydrogenation catalyst containing substantial carbonaceous deposits may be substantially restored by regenerating the catalyst and removing such accumulated carbonaceous deposits from the catalyst. Commonly, the carbonaceous deposits are removed and catalyst activity is regenerated by burning, under controlled conditions, in the presence of an oxygen containing gas. Such regeneration procedures are well known to those familiar with the regeneration of catalyst and need not be further described herein.

It may be convenient to employ a plurality of dehydrogenation reaction zones containing dehydrogenation catalysts, such that reaction zones are continuously available for use in the dehydrogenation process while other reaction zones are undergoing regeneration to remove carbonaceous deposits therefrom. Upon regeneration of the catalyst in a dehydrogenation reaction zone, such zone may be returned to service in the dehydrogenation process and another zone may be removed from service for regeneration.

The following examples are presented to illustrate specific embodiments of the practice of this invention and are not to be interpreted as limitations upon the scope of this invention.

EXAMPLE 1

Preparation of [Ni]-OMS-2

A 2.0M $MnSO_4$ (Fluka) aqueous solution (approx. 26 mL) was added to a mixture of distilled deionized water (4 mL) and concentrated nitric acid (3 mL). The pH of the final mixture was about 1.0. An aqueous permanganate solution was prepared by dissolving $KMnO_4$ (Baker)(5.89 g) in water (100 mL). The $KMnO_4$ solution was slowly added to the MnSO$_4$ solution with vigorous stirring. A 1.5M NiSO$_4$ (Mallinkrodt) solution (1.5 mL) was added to the reaction mixture. Thereafter, the reaction mixture was refluxed at 100° C. for 24 hours. During the course of the reaction a black precipitate formed and was recovered by filtering and washing with water. The recovered solid was dried at 120° C. for 16 hours. The yield was 8.13 g. X-ray powder diffraction patterns of the product evidence the presence of (2×2) tunnel structures.

EXAMPLE 2

Preparation of [Ni]-OMS-1

A 0.10M NiCl$_2$ aqueous solution (8.0 mL) was added to a 0.5M MnCl$_2$ aqueous solution (60 mL) to result in the formation of a suspension. Thereafter, a 6M NaOH solution (75 mL) was added to the suspension. After that, about 60 mL of 0.20 M NaMnO was then added to the mixture slowly. The mixture was aged at room temperature for 1 week and then filtered and washed to remove Cl$^-$ and Na$^+$ ions and recover product. X-ray powder diffraction (XRD) patterns of the product showed a birnessite-like layered manganese oxide structure. The layered material was ion-exchanged with 1M MgCl$_2$ (500 mL) for 8 hours to provide a Mg$^{2+}$-exchanged layered material showing a buserite XRD pattern. The exchanged layered material was hydrothermally treated in an autoclave at 160° C. for 30 hours. The product was finally filtered and washed. XRD patterns of the product evidence the presence of (3×3) tunnel structures.

The following examples illustrate the laboratory scale dehydrogenation of n-hexane to n-hexene-1 and n-hexene-2. It should be understood that these examples are presented to demonstrate the utility of the OMS catalyst disclosed herein as a dehydrogenation catalyst. It should further be understood that the dehydrogenation process of this invention can be practiced on a commercial-scale in the manner disclosed hereinabove.

EXAMPLE 3

Dehydrogenation of n-Hexane on [Ni]-OMS-2

Fluid phase dehydrogenation of n-hexane in a pyrex glass reactor of internal diameter ¼" was conducted by loading [Ni]-OMS-2 (0.5 g) prepared in Example 1 into the reactor and charging n-hexane (7 g) in 2 h over the catalyst together with a stream of helium. The mole ratio of He/hexane in the charge varied between 2–8 and under the reaction conditions of 1 atm and 500° C. The reaction was monitored by injecting liquid effluent every 30 minutes for GC analyses. Liquid samples were subjected to GC/MS analysis. Results showed 19–25% n-hexene-1 and about 3% n-hexene-2 in the product. The overall selectivity to the mono-olefins was about 90–95% mole.

EXAMPLE 4

Dehydrogenation of n-Hexane on [Ni]-OMS-1

Fluid phase dehydrogenation of n-hexane in a pyrex glass reactor of internal diameter ¼" was conducted by loading [Ni]-OMS-1 (0.5 g) prepared in Example 2 into the reactor and charging n-hexane (7 g) in 2 h over the catalyst together with a stream of helium. The mole ratio of He/hexane in the charge varied between 2–8 and under the reaction conditions of 1 atm and 500° C. The reaction was monitored by injecting liquid effluent every 30 minutes for GC analyses. Liquid samples are also subjected for GC/MS analysis. Results showed 15–20% n-hexene-1 and about 3% n-hexene-2 in the product. The overall selectivity to the mono-olefins was about 80% mole.

What is claimed is:

1. A method of converting n-paraffin to n-olefin which comprises contacting n-paraffin with synthetic manganese oxide octahedral molecular sieve as catalyst under dehydrogenation conditions to provide n-olefin.

2. The method of claim 1 wherein the octahedral molecular sieve is OMS-1 and/or OMS-2.

3. The method of claim 1 wherein the octahedral molecular sieve is combined with a support.

4. The method of claim 3 wherein the support is alumina or silica.

5. The method of claim 1 wherein the octahedral molecular sieve corresponds to the general formula:

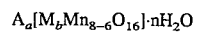

$$A_a[M_bMn_{8-b}O_{16}]\cdot nH_2O$$

wherein A is a +1, +2, +3 or +4 tunnel cation or combination thereof, $0 \leq a \leq 4$, M is a +1, +2, +3 or +4 framework-substituting metal cation or combination thereof, $0 \leq b \leq 8$ and $n \geq 0$.

6. The method of claim 5 wherein the tunnel cation is selected from the group consisting of alkali metals, alkaline earth metals and transition metals.

7. The method of claim 5 wherein the tunnel cation is selected from the group consisting of Li, Na, K, Cs, Mg, Ca, Ba, Co, Ni, Cu and Zn.

8. The method of claim 5 wherein the framework-substituting metal cation is a transition metal.

9. The method of claim 5 wherein the framework-substituting metal cation is selected from the group consisting of Mg, Fe, Co, Ni, Cu, Ti, V, Cd, Mo, W, Cr, Zn, La, Ir, Rh, Pd and Pt.

10. The method of claim 1 wherein the octahedral molecular sieve corresponds to the general formula:

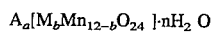

$$A_a[M_bMn_{12-b}O_{24}]\cdot nH_2O$$

wherein A is a +1, +2, +3 or +4 tunnel cation or combination thereof, $0 \leq a \leq 6$, M is a +1, +2, +3 or +4 framework-substituting metal cation or combination thereof, $0 \leq b \leq 12$ and $n \geq 0$.

11. The method of claim 10 wherein the tunnel cation is selected from the group consisting of alkali metals, alkaline earth metals and transition metals.

12. The method of claim 10 wherein the tunnel cation is selected from the group consisting of Li, Na, K, Cs, Mg, Ca, Ba, Co, Ni, Cu and Zn.

13. The method of claim 10 wherein the framework-substituting metal cation is a transition metal.

14. The method of claim 10 wherein the framework-substituting metal cation is selected from the group consisting of Mg, Fe, Co, Ni, Cu, Ti, V, Cd, Mo, W, Cr, Zn, La, Ir, Rh, Pd and Pt.

15. The method of claim 1 wherein the dehydrogenation conditions include a temperature ranging from about 100° to about 750° C.

16. The method of claim 1 wherein the dehydrogenation conditions include a temperature ranging from about 400° to about 650° C.

17. The method of claim 1 wherein the dehydrogenation conditions include pressure ranging from about 0.1 to about 100 atm.

18. The method of claim 1 wherein the dehydrogenation conditions include pressure ranging from about 0.2 to about 10 atm.

19. The method of claim 1 wherein the dehydrogenation conditions include a weight hourly space velocity ranging from about 0.1 to about 40 WHSV.

20. The method of claim 1 wherein the dehydrogenation conditions include a weight hourly space velocity ranging from about 0.2 to about 25 WHSV.

* * * * *

UNITED STATES PATENT AND TRADEMARK OFFICE
CERTIFICATE OF CORRECTION

PATENT NO. : 5,597,944
DATED      : Jan. 28, 1997
INVENTOR(S): Chi-Lin O'Young, et al It is certified that error appears in the above-indentified patent and that said Letters Patent is hereby corrected as shown below:

<u>IN THE ABSTRACT</u>:

Line 1 of the Abstract, "n-parrofins" should be --n-paraffins--.

Col. 1, line 12, "Carbons" should be --carbons--;

Col. 1, line 44, "Dev.1," should be --Dev1.--.

Col. 1, line 58, ".  cryptomelane" should be --, cryptomelane--.

Col. 7, line 19, "NaMnO" should be --NaMnO$_4$--.

Signed and Sealed this

Twentieth Day of May, 1997

Attest:

BRUCE LEHMAN

Attesting Officer    Commissioner of Patents and Trademarks